United States Patent [19]

Stark, Jr.

[11] 4,297,459

[45] Oct. 27, 1981

[54] CURABLE EPOXY RESINS

[75] Inventor: Charles J. Stark, Jr., Clifton Park, N.Y.

[73] Assignee: General Electric Company, Schenectady, N.Y.

[21] Appl. No.: 176,467

[22] Filed: Aug. 8, 1980

[51] Int. Cl.³ .............................................. C08G 59/68
[52] U.S. Cl. ..................................... 525/507; 525/523; 528/88; 528/92; 528/361; 528/408; 528/411
[58] Field of Search .................. 525/507, 523; 528/88, 528/92, 361, 408, 411

[56] References Cited

U.S. PATENT DOCUMENTS 2,962,410 11/1960 Kohn ................................. 428/371
3,776,978 12/1973 Markovitz ........................ 528/92 X
3,812,214  5/1974 Markovitz ................... 260/830 TW

*Primary Examiner*—Earl A. Nielsen
*Attorney, Agent, or Firm*—Peter A. Bielinski; James C. Davis, Jr.; Joseph T. Cohen

[57] ABSTRACT

Curable epoxy resin compositions which exhibit controllable cure rates and extended storage life are described which utilize allylethers of catechol as accelerators in combination with certain curing agents. These accelerators can be employed in single package curable epoxy resin compositions useful in molding and casting applications.

25 Claims, No Drawings

CURABLE EPOXY RESINS

This invention is concerned with novel, heat-curable, thermosetting epoxy resin compositions having improved shelf life and a cure rate which can be varied over a broad temperature range utilizing a cure accelerator derived from the reaction of catechol and its derivatives with a suitable alkyle halide. More particularly, the invention relates to a composition of matter comprising an epoxy resin, a curing agent, and an accelerator (or mixtures of such accelerators) selected from the compounds of the general formula

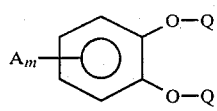 I.

where Q is independently selected from the class consisting of allyl radicals having from 3 to 15 carbon atoms, e.g., 2-methylallyl, 2-chloroallyl, oct-2-enyl, etc., or hydrogen, A is independently selected from the class consisting of monovalent alkyl (including aralykl) groups of from 1 to 8 carbon atoms (e.g., methyl, ethyl, benzyl, propyl, t-butyl, isopropyl, hexyl, 2-ethylhexyl, etc.), halogen (e.g., chlorine, bromine, etc.) and the nitro radical where A can be ortho-, meta-, or para- to either of the —OQ radicals and m is an integer from 0–2, inclusive, with the proviso that only one Q can be hydrogen.

The cure accelerators corresponding to formula I, may be prepared by reacting, in the presence of an inert solvent, such as toluene or benzene, a catechol of the formula

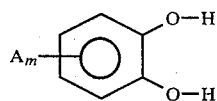 II.

with an unsaturated alkylene halide of the formula

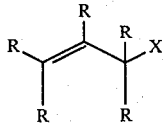 III where X is a halogen radical, e.g., chlorine, bromine, etc. and where R is independently selected from the class consisting ofhydrogen, monovalent alkyl (including aralkyl) groups of from 1 to 8 carbon atoms (e.g., methyl, ethyl, benzyl, propyl, isopropyl, hexyl, etc.); aryl (e.g., phenyl, napthyl, etc.); alkaryl, allyl, and halogen radicals, and A and m have the meanings above.

The determination whether 1 or both of the Q radicals in formula I will be an allyl derivative will depend on the molar concentrations of the ingredients as well as the concentrations of potassium carbonate which acts as a base to effect the reaction. For instance, if one desires to have only one allyl derivative and one OH group on the catechol derivative of formula I, one will normally employ 1 mol of an alkylene halide of formula III per mol of the catechol derivative of formula II. Where, however, it is desired to have two allyl derivatives attached through the oxygen directly to the aromatic nucleus of the catechol derivative of formula I, one will normally employ 2 mols of an alkylene halide of formula III per mol of the catechol derivative of formula II. Slight molar excesses of the alkylene halide of formula III may be employed as long as the formation of the desired catechol derivative of formula I is not jeopardized. The example described in the instant application will exemplify the molar relationship of ingredients required to make the catechol derivatives of formula I.

Examples of the alkylene halides which may be used in the preparation of the novel accelerators of the instant invention include, e.g., allyl bromide, allyl chloride, 3-chloro-1-butene, 2,3-dichloro-1-propene, 1,3-dichloro-2-butene, 1-chloro-2-pentene, 3-chloro-1-pentene [preparation disclosed by Turner and Gilbert, J.Am. Chem. Soc., Vol. 58, 1388 (1936)]; $\alpha,\delta$-dimethylallylchloride [disclosed by Goering and Jacobson, J.Am. Chem. Soc., Vol. 180, 3277 (1958)] and 4-bromo-2-octene, 1-bromo 2-pentene, 1-bromo-2-hexene, 1-bromo-2-heptene, [disclosed in J. Organic Chem., Vol. 2, 381 (1938)], etc.

Epoxy resin compositions, heretofore have been utilized for example, as electrical insulation for electrical conductors. The cure rate of the epoxy resins has previously been of prolonged duration, e.g., often as long as 10 to 15 hours at 160°, especially in casting applications, significantly delaying utilization of said epoxy resins in a broad range of applications. Moreover, the rate of cure for epoxy resin compositions heretofore have been controlled by the selection of a suitable hardener and an accelerator which generally dictated the temperature and time required to effect curing of the epoxy composition. In the past, accelerating the cure of the resins has often been at the expense of the storage stability at ambient temperatures. In general, there has not been a simple and satisfactory means available on a commercial basis to provide for an epoxy resin formulation that exhibits a stable shelf life at ambient temperature for a desired time and yet can be made to cure rapidly when required at elevated temperatures.

It is an object of the present invention to provide a thermosetting epoxy resin composition, the reactivity of which can be controlled over a very wide range, i.e., from stability for periods of up to 1 month or more to gelation and ability to cure rapidly at elevated temperatures, often lower than are usually required.

It is an additional object of this invention to provide epoxy resin compositions containing cure accelerators which impart desirable physical properties, including favorable chemical and electrical properties in the resultant heat-cured epoxy resin.

The term "epoxy resins" is intended to include those selected from both glycidyl and non-glycidyl ether epoxides containing more than one 1,2-epoxy groups per molecule.

Such non-glycidyl ether cycloaliphatic epoxides are characterized by the absence of the ether oxygen bond, i.e., —O—, near the epoxide group, and are selected from those which contain a ring structure as well as more than one epoxide group in the molecule. The epoxide group may be part of the ring structure or may be attached to the ring structure. These epoxides may also contain ester linkages. These ester linkages are generally not near the epoxide group and are relatively unreactive, therefore, these type materials are properly characterized as cycloaliphatic epoxides. These epoxides are generally prepared by epoxidizing unsaturated aliphatic hydrocarbon compounds, such as cyclic-olefins, using hydrogen peroxide or peracids such as peracetic acid and perbenzoic acid.

Other epoxy resins which may be employed in this invention such as 1,2-epoxy resins having more than one epoxy group per molecule include cycloaliphatic epoxy resins such as 3,4-epoxycyclohexylmethyl-(3,4-epoxy)-cyclohexane carboxylate (sold under the trademarks ERL 4221 by Union Carbide Co. or Araldite CY 179 by Ciba Products Company), bis(3,4-epoxy 6-methylcyclohexylmethyl) adipate (sold under the trademarks ERL 4289 by Union Carbide Co. or Araldite CY 178 by Ciba Products Company), bis (2,3-epoxycyclopentyl) ether resins (sold under the trademark ERL 4205 by Union Carbide Company), 2-(3,4-epoxy)cyclohexyl-5-, and 5-spiro (3,4-epoxy)-cyclohexane-m-dioxane, (sold under the trademark Araldite CY 175 by Ciba Products Company), etc.

Glycidyl ether based epoxy resins suitable for use according to the present invention include glycidyl ethers of phenolic epoxy resins such as liquid or solid bisphenol-A diglycidyl ether epoxy resins (such as those sold under trademarks as Epon 826, Epon 828, Epon 830, Epon 1001, Epon 1002, Epon 1004, etc., by Shell Chemical Company, phenol-formaldehyde novolac polyglycidyl ether epoxy resins (such as those sold under the trademarks DEN 431, DEN 438, and DEN 439 by Dow Chemical Company), and digylcidyl hexahydrophthalate (Araldite CY 183 made by Ciba Products Company); and flame retardant epoxy resins such as halogen-containing bisphenol-A diglycidyl ether epoxy resins (e.g., DER 542 and DER 511 which have bromine contents of 44–48 and 18–20%, respectively, and are made by Dow Chemical Company).

The foregoing epoxy resins are well known in the art and are set forth, for example, in many patents including U.S. Pat. Nos., 2,324,483, 2,444,333, 2,494,295, 2,500,600, and 2,511,913. The combined stabilizers and curing agents used in the practice of this invention are not only effective with various epoxy resins and mixtures of epoxy resins, but they are also effective in mixtures containing reactive and nonreactive epoxy diluents (or extenders), epoxy flexibilizers and fillers. There are many epoxy resin curing agents in use. Among the most common are the aromatic polyamines, aliphatic polyamines and their adducts, carboxylic acid anhydrides, polyamides and catalytic curing agents, as, for example, tertiary amines, imidazoles, BF$_3$ monoethylamine, and dicyanodiamide.

In addition, there are metal acetylacetonates in which the metal is aluminum, barium, beryllium, cadmium, calcium, cerous, chromic, cobaltic, cobaltous, cupric, ferric, ferrous, lead lithium, magnesium, manganic, molybdenum, nickel, potassium, titanium, zinc, zirconium, etc.

Phenolic cure accelerators are frequently used in conjunction with an initiator in the curing of epoxy resins. Among the more common accelerators are bisphenol-A [i.e., 2,2-bis (4-hydroxyphenyl) propane], catechol, resorcinol, and hydroquinone. Other phenolic accelerators include halogenated phenols such as ortho-, meta, and parachlorophenols or bromophenols. However, such types of accelerators either accelerate too slowly for many applications or tend to affect adversely the stability at room temperature of the resins in which they are incorporated.

The epoxy resin compositions of the present invention were unexpectedly found to exhibit enhanced storage stability in that the compositions did not spontaneously cure or gel at room temperature (25°–35° C.) during prolonged storage. As previously noted, the curing rate of epoxy resin compositions can be tailored to cure over a time span of from about one minute to several hours based on the resin or resin mixture selected, the amount and type of accelerator utilized in relation to the cure temperature chosen, etc. Further blends of epoxy resins such as ERL 4221 epoxy resin/ECN 1235 epoxy cresol novolac resin, or glycidyl ether and glycidyl ester epoxy resins may be cured using the accelerators of general formula I.

The curable epoxy resin compositions comprising a suitable epoxy resin or epoxy resin mixture, a titanate or zirconate curing agent and an accelerator corresponding to formula I can be heat cured at a temperature of from 50° C. to 200° C., and advantageously cured at a temperature of from 100° C. to 175° C., to obtain the heat-cured product.

The composite heat curable epoxy resins of the present invention are characterized by good shelf life thus making them available in the form of a one-component, ready to use package, not requiring the blending of ingredients immediately prior to utilization. The epoxy resin compositions generally consist of a mixture of a resin, an organic titanate or zirconate cure initiator or curing agent and an accelerator of formula I.

Some of the application in which the curable compositions of the present invention can be used, are, for example, protective coatings, liquid injection molding compounds, wire insulation, encapsulation of electronic components pultrusion, laminates, bulk molding compounds (BMC), e.g., as housings for motors, grills for automobiles, etc.

The organic titanate initiators which are added to the epoxy resin composition to initiate the cure of the epoxy resins include chelated titanates such as acetylacetonate titanate, lactate titanate, triethanolamine titanate, polyhydroxystearate titanate, a glycolate titanate (e.g., tetraoctyl, glycol titanate containing approximately 7.8% Ti and sold under the trademark Tyzor OG by E. I. du Pont de Nemours and Company or di-n-butyl hexylene glycol titanate), and nonchelate titanates such as tetraisopropyl titanate (TPT), tetrabutyl titanate, polymerized tetrabutyl titanate, and tetrakis (2-ethylhexyl) titanate (TOT). In general, the chosen titanate should be present in the mixture in a concentration between 0.03 and 15% by weight, based on the weight of the epoxy resin, with optimum cure rates generally being obtained utilizing titanate concentrations between 1 to 10%, by weight, of the epoxy resin. The amount of curing agent used will depend on such factors as type of epoxy resin used, temperature at which cure is to take place, type of accelerator used, etc.

In place of organic titanates, organic zirconate curing agents can be used for the curing of the epoxy resins, and these include, for example, zirconium acetylacetonate, zirconium-tert-butoxide, zirconium hexafluroacetylacetonate, zirconium naphthenate (sold by Witco Chemical Company, Incorporated), zirconium propoxide and zirconium isopropoxide (sold by Ventron Corporation), etc.

Such zirconate curing agents can be used in amounts similar to those for the titanate curing agents, that is, the chosen zirconate should be present in a concentration between 0.01 to 15% by weight, based on the weight of the epoxy resin, with a preferred concentration between 1.10 to 10% by weight, of the epoxy resin.

In order that those skilled in the art may better understand how the present invention may be practiced, the following examples are given by way of illustration and not by way of limitation. All parts are by weight unless otherwise indicated.

EXAMPLE 1

An accelerator having the formula

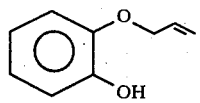
IV.

was prepared following substantially the procedure disclosed in Indian Journal of Chemistry, Vol. 2, pp. 323–326 (1964). In a 1 liter flask fitted with a reflux condenser was introduced 250 parts of dry acetone and a few boiling chips. Thereafter, a mixture of 75 parts catechol, 247 parts allyl bromide and 282 parts potassium bromide was added to the flask with stirring. The mixture was heated to reflux for 12 hours at 56° C. under an atmosphere of nitrogen and when the reaction was completed, the mixture was cooled and the solids filtered from solution. The liquid phase was condensed by rotovap and the residue distilled at 2 Torr to yield 98 parts of the accelerator described above.

EXAMPLE 2

A mixture of 100 parts Epon 828, 1.5 parts Tyzor TPT and 4.0 parts of the accelerator of Example 1 was prepared. The gelation time of this composition was measured with a Sunshine Gel Meter (Sunshine Scientific Instruments Co., Philadelphia, Pa.). The following Table I shows the gel times of the aforesaid composition at varying temperatures:

TABLE I

| Test No. | T° C. | Gel Time (min.) |
|---|---|---|
| 1 | 50 | 4100.9 (~3 days) |
| 2 | 130 | 7.3 |
| 3 | 150 | 3.1 |
| 4 | 170 | 1.7 |

For comparison, when the accelerator was eliminated, the otherwise same composition did not cure even when heated at 150° C. in excess of 24 hours. To show that storage stability is diminished when an unsubstituted catechol accelerator is used in lieu of catechol derived accelerators of the present invention, another test was conducted wherein a mixture of 100 parts Epon 828, 1.5 parts Tyzor TPT and 4.0 parts catechol was prepared. The gelation time at 50° C. of this composition measured with the aforementioned gel equipment was approximately 3.0 minutes indicating clearly the enhanced storage stability possible by the practice of my invention.

EXAMPLE 3

A mixture of 100 parts Epon 828, 3.37 parts Tyzor OG and 4.0 parts of the accelerator prepared in Example 1 was prepared. The following Table II shows the gel times of the aforesaid composition at varying temperatures as measured with a Sunshine Gel Meter:

TABLE II

| Test No. | T° C. | Gel Time (min.) |
|---|---|---|
| 5 | 50 | No gel after 20 days |
| 6 | 150 | 15.0 |
| 7 | 170 | 5.5 |

EXAMPLE 4

A thermosetting epoxy resin composition was prepared by mixing 100 parts Epon 828 with 1.54 parts Tyzor TPT and 5.14 parts of an accelerator of the formula

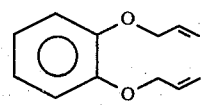
V.

(prepared similarly as the accelerator of Example 1, by reacting 1 molar equivalent of catechol with 3 molar equivalents of allylbromide in the presence of $K_2CO_3$ and acetone). The following Table III shows the gel times of the aforesaid composition at varying temperatures as measured with a Sunshine Gel Meter:

TABLE III

| Test No. | T° C. | Gel Time (min.) |
|---|---|---|
| 8 | 50 | No gel after 19 days |
| 9 | 150 | 100 |
| 10 | 160 | 56.1 |
| 11 | 170 | 29.8 |
| 12 | 180 | 13.9 |
| 13 | 190 | 8.4 |
| 14 | 200 | 4.5 |

EXAMPLE 5

Tests 15–17 of Table IV show the heat deflection temperatures (HDT) for tests run on resin-accelerator mixtures cured using the composition of Example 2 but substituting other titanate cure initiators as indicated. The equivalent weights of the ingredients and titanates used were substantially the same as in Example 2. The mixtures of tests 15–17 were mixed at room temperature and poured into a mold. The mold was then placed in an oven, where it was maintained for 24 hours at the temperature indicated. Subsequently, the mold was removed and disassembled. The molded parts obtained were machined to produce samples of 4.75"×0.5"×0.25" for measuring heat deflection temperatures. The temperatures required to produce a 10 mil deflection under 264 psi were measured and recorded as indicated in Table IV.

TABLE IV

| Test No. | Oven °C. | Tyzor | Accelerator | Parts Accelerator | HDT (°C.) |
|---|---|---|---|---|---|
| 15 | 150 | TPT | Example 1 | 1.50 | 102 |
| 16 | 150 | OG | Example 1 | 3.37 | 91 |
| 17 | 170 | OG | Example 1 | 3.37 | 94 |

EXAMPLE 6

A thermosetting epoxy resin composition is prepared by mixing 100 parts Epon 828 with 3,4 parts Tyzor OG and 5.0 parts of an accelerator having the formula

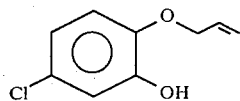   VI.

(prepared by reacting 1 molar equivalent of 4-chlorocatechol with 1 molar equivalent of allyl bromide). When this mixture of ingredients using the accelerator of formula VI is tested as in the preceding examples, it will be found that the storage stability of the uncured material is enhanced and the rate of cure at elevated temperature is accelerated.

EXAMPLE 7

A thermosetting epoxy resin composition is prepared by mixing 100 parts Epon 828 with 3.37 parts Tyzor OG and 5.6 parts of an accelerator having the formula

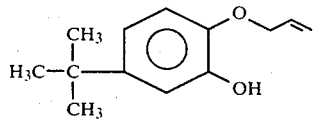   VII.

(prepared by reacting 1 molar equivalent of t-butyl catechol with 1 molar equivalent allylbromide in the presence of $K_2CO_3$ and acetone). When this mixture of ingredients using the accelerator of formula VII is tested as in the preceding examples, it will be found that the storage stability of the uncured material is enhanced and the rate of cure at elevated temperatures is accelerated.

What I claim as new and desire to secure by Letters Patent of the United States is:

1. A composition of matter comprising an epoxy resin, a cure initiator, and an accelerator of the general formula

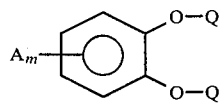

where Q is independently selected from the class consisting of allyl radicals having from 3 to 15 carbon atoms, or hydrogen radicals and A is independently selected from the class consisting of monovalent alkyl (including aralkyl) groups of from 1 to 8 carbon atoms, halogen and the nitro radical, where A can be ortho-, meta-, or para- to either of the —OQ radicals, and m is an integer from 0 to 2, inclusive, with the proviso that only one Q can be hydrogen.

2. A composition of matter as in claim 1, wherein the cure initiator is a titanium or zirconium ester.

3. A composition of matter as in claim 1 wherein the accelerator has the formula

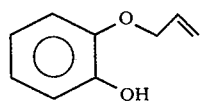

4. A composition of matter as in claim 1 wherein the accelerator has the formula

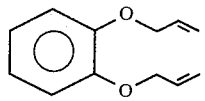

5. A composition of matter as in claim 1, wherein the accelerator has the formula

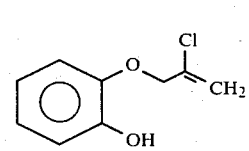

6. A composition of matter as in claim 1, wherein the accelerator has the formula

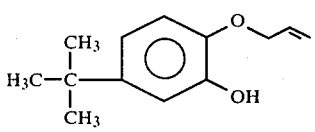

7. A composition of matter as in claim 1 wherein the accelerator has the formula

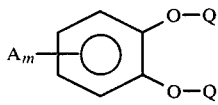

8. A composition of matter as in claim 1 wherein the cure initiator is a zirconium ester and the accelerator has the general formula

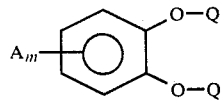

where Q is independently selected from the class consisting of allyl radicals having from 3 to 15 carbon atoms or hydrogen radicals, and A is independently selected from the class consisting of monovalent alkyl (including aralkyl) groups of from 1 to 8 carbon atoms, halogen and the nitro radical, where A can be ortho-, meta-, or para- to either of the —OQ radicals, and m is an integer from 0 to 2 inclusive, with the proviso that only one Q can be hydrogen.

9. A composition of matter as in claim 1, wherein the cure initiator is a titanium ester and the accelerator has the general formula

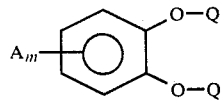

where Q is independently selected from the class consisting of allyl radicals having from 3 to 15 carbon atoms or hydrogen radicals and, A is independently selected from the class consisting of monovalent alkyl (including aralkyl) groups of from 1 to 8 carbon atoms, halogen and the nitro radical, where A can be ortho-, meta-, or para- to either of the —OQ radicals, and m is an integer from 0 to 2, inclusive, with the proviso that only one Q can be hydrogen.

10. A composition of matter as in claim 1 wherein the cure initiator is a titanate ester and the accelerator is a compound of the formula

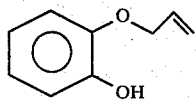

11. A composition of matter as in claim 1 wherein the cure initiator is a titanate ester and the accelerator is a compound of the formula

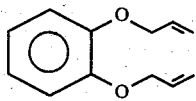

12. A method for curing an epoxy resin which comprises (1) forming a mixture of ingredients comprising an epoxy resin, a cure initiator, and an accelerator of the general formula

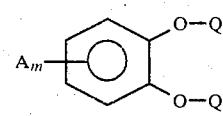

where Q is independently selected from the class consisting of allyl radicals having from 3 to 15 carbon atoms or hydrogen radicals and, A is independently selected from the class consisting of monovalent alkyl (including aralkyl) groups of from 1 to 8 carbon atoms, halogen and the nitro radical, where A can be ortho-, meta-, or para to either of the —OQ radicals, and m is an integer from 0 to 2, inclusive, with the proviso that only one Q can be hydrogen, (2) heating the aforesaid mixture of ingredients at a temperature and for a time sufficient to effect curing of said epoxy resin.

13. A method for curing an epoxy resin according to claim 12, wherein the cure initiator is a titanium ester.

14. A method for curing an epoxy resin according to claim 12, wherein the cure initiator is a zirconium ester.

15. The heat cured product of claim 1.
16. The heat cured product of claim 2.
17. The heat cured composition of claim 3.
18. The heat cured composition of claim 4.
19. The heat cured composition of claim 5.
20. The heat cured composition of claim 6.
21. The heat cured composition of claim 7.
22. The heat cured composition of claim 8.
23. The heat cured composition of claim 9.
24. The heat cured composition of claim 10.
25. The heat cured composition of claim 11.

* * * * *